United States Patent
Lobregt et al.

[11] Patent Number: 6,078,699
[45] Date of Patent: *Jun. 20, 2000

[54] COMPOSING AN IMAGE FROM SUB-IMAGES

[75] Inventors: Steven Lobregt; Alexander H. W. Van Eeuwijk, both of Eindhoven, Netherlands

[73] Assignee: U.S. Philips Corporation, New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/911,077

[22] Filed: Aug. 14, 1997

[30] Foreign Application Priority Data

Aug. 21, 1996 [EP] European Pat. Off. ............... 96202325

[51] Int. Cl.$^7$ ........................................ G06K 9/36
[52] U.S. Cl. ........................................ 382/284; 382/294
[58] Field of Search ........................................ 382/131, 294, 382/284, 130, 132, 302, 103; 348/584, 586; 345/435; 378/98.7, 98.12; 347/176

[56] References Cited

U.S. PATENT DOCUMENTS

| | | |
|---|---|---|
| 3,905,045 | 9/1975 | Nickel ........................................ 382/130 |
| 4,870,692 | 9/1989 | Zuiderveld et al. ................... 378/98.12 |
| 5,027,413 | 6/1991 | Barnard ................................... 382/103 |
| 5,140,341 | 8/1992 | Fiscella et al. ........................... 347/176 |
| 5,602,896 | 2/1997 | Diepstraten ............................... 378/98.7 |
| 5,649,032 | 7/1997 | Burt et al. ................................. 382/284 |

FOREIGN PATENT DOCUMENTS

| | | | |
|---|---|---|---|
| WO9410653 | 5/1994 | European Pat. Off. | G06K 9/36 |
| 0655861A1 | 11/1994 | European Pat. Off. | H04N 5/32 |

*Primary Examiner*—Yon J. Couso
*Attorney, Agent, or Firm*—Dwight H. Renfrew

[57] ABSTRACT

Sub-images of an e.g. elongate scene are merged so as to form combined first and second portions on the basis of individual shifts of successive sub-images relative to the elongate scene. The first combined portion is distorted, notably compressed or expanded, on the basis of the dimensions of the first and second combined portions. The distorted first combined portion is merged with the combined second portion so as to form the composite image. The sub-images are formed, for example by irradiating a patient by means of an X-ray beam in different positions. For example, the distorted combined first portion shows a scale graduation and the combined second portion contains anatomic information of a patient.

13 Claims, 2 Drawing Sheets

COMPOSING AN IMAGE FROM SUB-IMAGES

BACKGROUND OF THE INVENTION

1. Field of the Invention

The invention relates to an image composition method in which a first shift value for a mutual shift of successive sub-images is derived from first portions of sub-images and respective first portions of successive sub-images are merged, on the basis of the first shift value so as to form a combined first portion.

2. Description of Related Art

A method of this kind is known from European Patent Application EP 0 655 861.

The composition of an image from sub-images is generally used to form a composite image of an elongate scene which is too long to be reproduced in one operation. In medical X-ray diagnostics such a situation occurs notably for peripheral X-ray angiography where X-ray images are formed of blood vessels in the limbs, but also, for example, when an image of the spinal column is made. Using a contemporary X-ray examination apparatus it is difficult or even impossible to form an X-ray image of the complete region of an arm or a leg of a patient to be examined in one exposure. A number of successive X-ray images of portions of the region to be examined are formed, which images together cover the entire region. An X-ray image intensifier forms optical images from the X-ray images and an image pick-up apparatus, for example a television camera, derives image signals from the optical images. The image signals represent the sub-images used to form the composite image.

The known method includes a procedure for deriving a mutual shift of successive sub-images from correlation between pixel values of overlapping portions of successive sub-images. Upon combination of the sub-images, pixel values of mutually overlapping portions of successive sub-images and those relating to the same position in the elongate scene are interpolated so as to form pixel values of the composite image. The known method is successful notably in preventing mutual differences in brightness values in overlapping portions of successive sub-images from introducing disturbances in the composite image. However, in the case of parallax in the sub-images, the known method is not adequate in counteracting resultant disturbances in the composite image. Notably when X-ray images are formed, shadow images are produced in which objects situated at different distances from the X-ray source are imaged in the same image plane. Due to parallax, differences occur in the images of objects situated at different distances from the X-ray source and in different sub-images. In the known method such differences still cause disturbances in the composite image of the elongate scene which shows, for example the vascular system in a leg of the patient.

SUMMARY OF THE INVENTION

It is an object of the invention to provide a method of composing an image from sub-images in which disturbances in the composite image which are due to the merging of the sub-images are counteracted better than in the known method.

This object is achieved by means of a method according to the invention which is characterized in that a second shift value for a mutual shift of successive sub-images relative to the scene is derived from second portions of sub-images, respective second portions of successive sub-images are merged on the basis of the second shift value so as to form a combined second portion, the combined first portion is distorted on the basis of dimensions of the combined first and second portions, and the composite image is formed on the basis of the distorted combined first portion thus obtained and the combined second portion.

Separate first and second portions of successive sub-images often have different mutual shifts relative to the elongate scene. For example, parallax is one cause of such differences. If the sub-images contain image information of X-ray images, or if the sub-images are X-ray images, parallax occurs because individual portions of the elongate scene are situated at different distances from the X-ray source and are viewed in different directions from different positions of the X-ray source. In peripheral X-ray angiography differences exist in the distances between the X-ray source and, for example the vascular system in an arm or a leg and bones in the arm or leg of a patient. Because of these differences in distances and directions from the X-ray source, the mutual shifts of successive sub-images differ for individual portions of said sub-images. The first and second shift values are derived in order to take into account differences between mutual shifts of individual portions of successive sub-images. The first and the second shift value represent the mutual shift of first and second portions of successive sub-images, respectively, relative to the elongate scene. The first and second portions of the sub-images are preferably chosen such that the mutual shifts of successive sub-images is substantially constant within such a first or second portion, i.e. such that the parallax remains the same within such a first or second portion.

The mutual shift of sub-images represents the relative positions of the sub-images corresponding the relative positions of features in a scene which is (partially) imaged in the sub-images.

The first and second shift values are separately derived from the first and second portions as is known per se from European Patent Application EP 0 655 861, for example on the basis of correlations between pixel values of corresponding positions in overlapping portions of first or second portions of successive sub-images. The first and second combined portions per se are substantially free from disturbances due to the merging of the portions of sub-images, but the differences between the first and second shift values introduce a difference between the dimensions of the first and second combined portions. When an elongate scene is reproduced, differences occur notably between the lengths of the first and second combined portions. The distortion is chosen to be such that dimensions of the distorted first combined portion and the second combined portion relate to dimensions of corresponding portions in the elongate scene in precisely the same way. Because of the distortion of the first portion on the basis of the lengths of the first and second combined portions it is achieved notably that the distorted first combined portion has substantially the same dimension as the combined second portion. It is thus achieved that the composite image is substantially free from disturbances due to the merging of the sub-images. Notably disturbances relating to differences in parallax between different portions of the sub-images are avoided, for example when these sub-images represent image information from X-ray shadow images. The composite image reproduces in a single image essentially the entire elongate scene without disturbances. Because hardly any disturbances occur, small details are clearly visible in the composite image. When the invention is used for peripheral X-ray angiography, the method produces a composite image of high diagnostic quality which shows a substantial part of the vascular system of the patient. For example, a composite image can be formed which reproduces substantially the entire vascular system of the legs of a patient, so from the groin down to the feet. The composite image is also suitable for accurate extraction of dimensions in the scene shown. Notably the dimensions of parts of limbs, such as bones, dimensions of vertebrae or distances between vertebrae, can be derived from the composite image.

Notably, the sub-images represent a scene that is larger than the largest scene that can be picked-up by a relevant imaging system. For example the scene is a part of a patient that is larger a region of a relevant x-ray examination apparatus can form an x-ray image in a single irradiation. In particular the method according to the invention is advantageously employed for assembling sub-images of an elongate scene, like a set of x-ray images of a patient's arm or leg.

A preferred version of an image composition method according to the invention is characterized in that the combined first portion is distorted on the basis of a ratio of dimensions of the combined first and second portions.

The ratio of the dimensions of the first and second combined portions represents an instantaneous mutual deviation of dimensions of the individual combined first and second portions.

A further preferred version of an image composition method according to the invention is characterized in that the method includes distortion of the combined first portion by compression or expansion in the longitudinal direction of the combined first portion.

These individual combined portions represent portions of substantially the same dimensions in the elongate scene. Distortion of the first portion on the basis of the ratio of the dimensions of the first and second combined portions offers very good results for the composite image. It has been found that in many practical cases expansion or compression of the first combined portion in the longitudinal direction on the basis of said ratio suffices to ensure that the length of the distorted (expanded or compressed) first combined portion becomes substantially equal to the length of the combined second portion. Evidently, it is also possible to distort the first as well as the second combined portion to some extent, one portion being compressed while the other is expanded, in order to make the lengths of the distorted combined portions substantially equal.

A further preferred version of an image composition method according to the invention is characterized in that said first portions contain mainly image information, and that said second portions represent mainly a scale graduation.

In many cases, notably in peripheral X-ray angiography, it is advantageous to add a scale graduation to the elongate scene. Such a scale graduation is taken up, for example in an X-ray absorbing ruler mounted on or underneath the patient table. Such a ruler may also be incorporated in the patient table. An X-ray absorbing ruler is known per se from European Patent Application EP 0 655 861, but the method described therein does not utilize such a ruler for measuring distances in the elongate scene, but merely for forming correlations between overlapping portions of successive sub-images. The method according to the invention forms a composite image of the elongate scene without any or with hardly any disturbances neither in the reproduction of the elongate scene nor in the reproduction of the scale graduation. Consequently, the composite image is suitable for extracting exact dimensions in the elongate scene by means of the substantially fault-free or completely fault-free reproduction of the scale graduation.

A further preferred version of an image composition method according to the invention is characterized in that first and/or second portions are selected from the sub-images on the basis of visual inspection of image information of the sub-images.

In practical situations differences occur in the shift between individual sub-images in various portions of these sub-images. The portions for which the shifts differ, for example due to parallax, are often difficult to predict. Inspection of image information of the sub-images can reveal where different shifts have occurred. Such an inspection can be performed, for example on an image formed by the merging of sub-images while taking into account only a single value for individual pairs of successive sub-images.

The same advantages of the method according to the invention can be achieved if there are more than two portions having different shift values in individual sub-images and/or if the composite image is formed from more than two sub-images.

The method can also be used when shifts in different directions occur between individual pairs of sub-images. In that case lengths of combined portions of individual pairs of sub-images extend in different directions.

A further preferred version of an image composition method according to the invention is characterized in that a mutual shift relative to the scene is derived from individual portions of respective sub-images, corresponding portions of respective sub-images are merged so as to form combined portions on the basis of the mutual shift of the relevant sub-images, combined portions are distorted so as to form distorted portions, and distorted portions are merged so as to form a composite image.

Because of the distortion of the first combined portion it is achieved that the composite image will not contain disturbances caused by the fact that the sub-images wherefrom the first and second combined portion are formed are mutually shifted over different distances relative to the scene reproduced. An individual sub-image can be subdivided into many separate portions for which a respective shift value and distortion are derived. Consequently, disturbances are avoided practically throughout the composite image and there will be substantially no distortion. On the basis of the individual shift values an estimate can be made of the depth of what is reproduced in the individual portions in the elongate scene.

The invention also relates to an image composition method in which a first combined image is composed from sub-images, a second combined image is composed from sub-images, the first combined image is distorted on the basis of the dimensions of the first and the second combined image, and the distorted first combined image and the second combined image are merged so as to form a composite image.

The method according to the invention is performed preferably by means of an image processing system which is arranged to derive the first and second shift values, to form combined portions from portions of successive sub-images, to distort a combined portion and to form the composite image by merging on the basis of the distorted combined first portion and the combined second portion. Such an image processing system preferably performs the method on image signals, such as electronic video signals, representing brightness values of the sub-images. An image processing system for carrying out the method according to the invention can be provided in the form of a suitably programmed computer or a (micro)processor with integrated circuits suitably designed to perform the steps of the method on image signals.

These and other aspects of the invention will become apparent from and will be elucidated with reference to the following embodiments and the associated drawing; therein

DETAILED DESCRIPTION OF THE PREFERRED EMBODIMENTS

Figure 1:
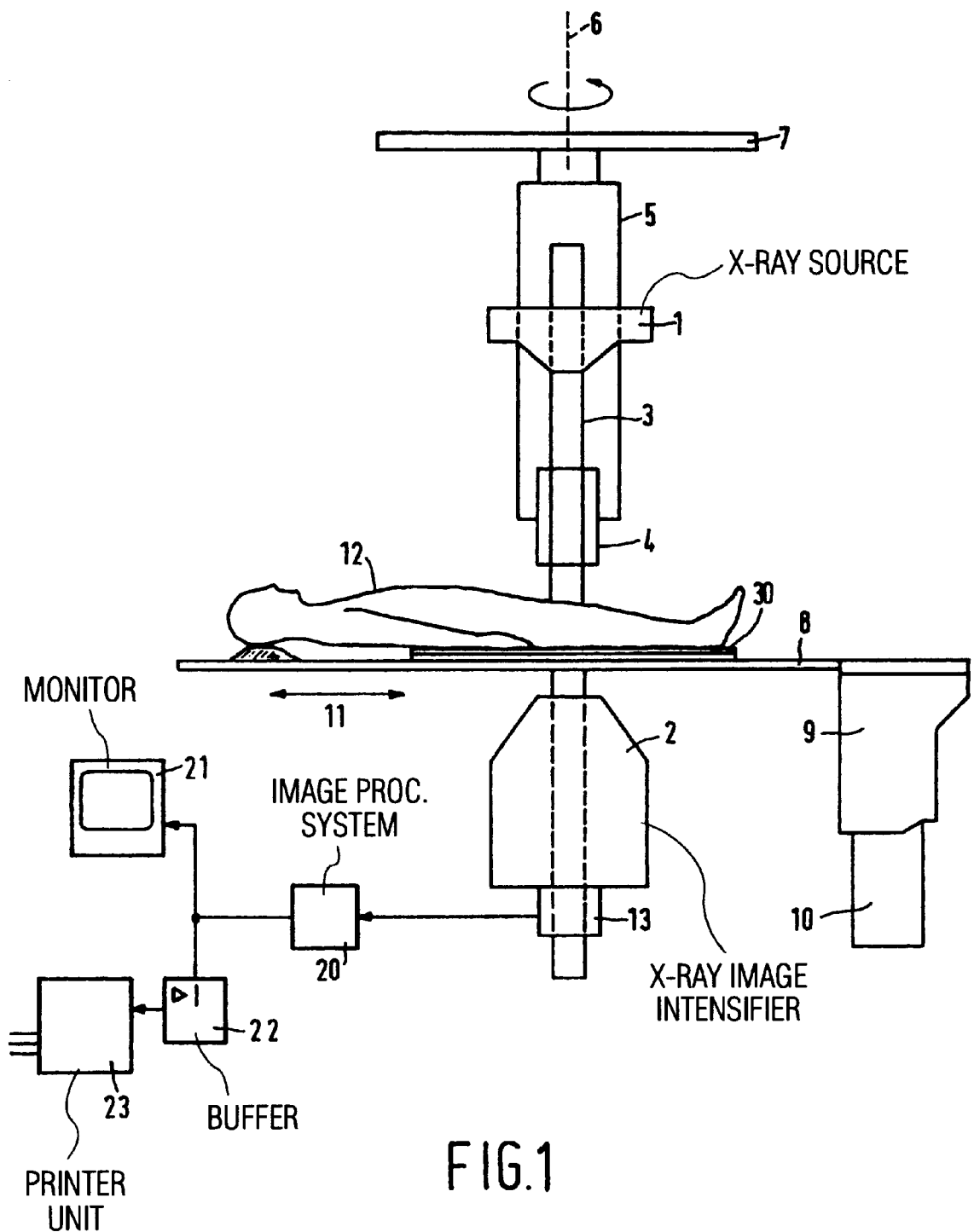
FIG. 1 is a side elevation of an X-ray examination apparatus for forming X-ray images subjected to the method according to the invention.

FIG. 1 is a side elevation of an X-ray examination apparatus for forming X-ray images of a patient to be examined which are subjected to the method according to the invention. An X-ray source 1 and an X-ray detector 2, for example an X-ray image intensifier, are connected to a carrier 3, for example a C-arm. The C-arm 3 is movably connected to a vertical support 5 by means of a sleeve 4. The vertical support is rotatable around a substantially vertical axis of rotation 6 and is suspended from a set of rails 7 mounted on the ceiling of the room in which the X-ray examination apparatus is installed. A patient table 8 is movably connected to a frame 9 which is mounted on a column 10. The frame 9 can be moved up and down the column 10 so as to adjust the height of the table relative to the X-ray source 1. The patient table 8 is movable relative to the frame in order to enable displacement in the longitudinal direction 11 of the patient table 8 on which the patient is arranged. In this configuration the patient is positioned on the patient table 8 during the examination and the frame 9 with the X-ray source 1 and the X-ray detector 2 and the patient table 8 with the patient 12 are displaced relative to one another, in the longitudinal direction 11 separate X-ray images being formed in separate mutual positions. It is alternatively possible for the patient to stand upright during the examination, the frame 9 with the X-ray source 1 and the X-ray detector 2 then being movable vertically along the patient.

An X-ray image is formed by irradiating (a part of) the patient to be examined by means of an X-ray beam emitted by the X-ray source 1. Because of local differences in X-ray absorption within the patient an X-ray image is formed on an entrance screen of the X-ray image intensifier 2 which derives an optical image from the X-ray image, which optical image appears on an exit window. The optical image is picked up by a television camera 13. The television camera supplies an image signal in the form of an electronic video signal. The signal levels of this image signal represent brightness values in the X-ray image. Individual X-ray images act as sub-images which are combined so as to form a composite image according to the invention. For individual X-ray images the image signals are applied to an image processing system 20 which merges the sub-images represented by said image signals, so as to form a composite image. The image processing system applies an image signal for said composite image to a monitor 21 on which the image information of the merged sub-images is displayed, but the image signal for said composite image can alternatively be applied via a buffer 22 to a printer unit 23, for example a so-called laser camera, which prints the image information on a transparency or on paper.

For peripheral X-ray angiography, i.e. the visualization of blood vessels in an arm or a leg of a patient, a contrast liquid is injected into an artery and the progression of contrast liquid through the vascular system is monitored by displacing the patient table 8 with the patient in conformity with the movement of the contrast fluid. It is equally well possible to displace the support 5 with the X-ray source 1 and the X-ray detector 2 along the patient 12. A number of X-ray images are formed during the movement of the patient relative to the X-ray source and the X-ray detector, that is to say always of the region just reached by the contrast fluid. The X-ray images together contain image information concerning the blood flow in the vascular system of the relevant limb. The composite image formed from the sub-images according to the invention shows the image information in a single composite image which can be more readily evaluated for diagnosis by the radiologist than the individual sub-images.

The patient table 8 is provided with an X-ray absorbing scale graduation 30, for example in the form of a ruler. The ruler is also reproduced in the X-ray images of the patient. As a result, dimensions of anatomic structures, such as blood vessels or bone structures, can be accurately derived from the X-ray images. Details of rulers which are particularly suitable for use in X-ray diagnostics, notably in peripheral X-ray angiography, so as to establish correlations between sub-images are known per se from European Patent Application EP 0 655 861. Such a ruler may be provided with a scale graduation so that the dimensions of portions of the anatomy of the patient to be examined can be readily and accurately read.

Figure 2:
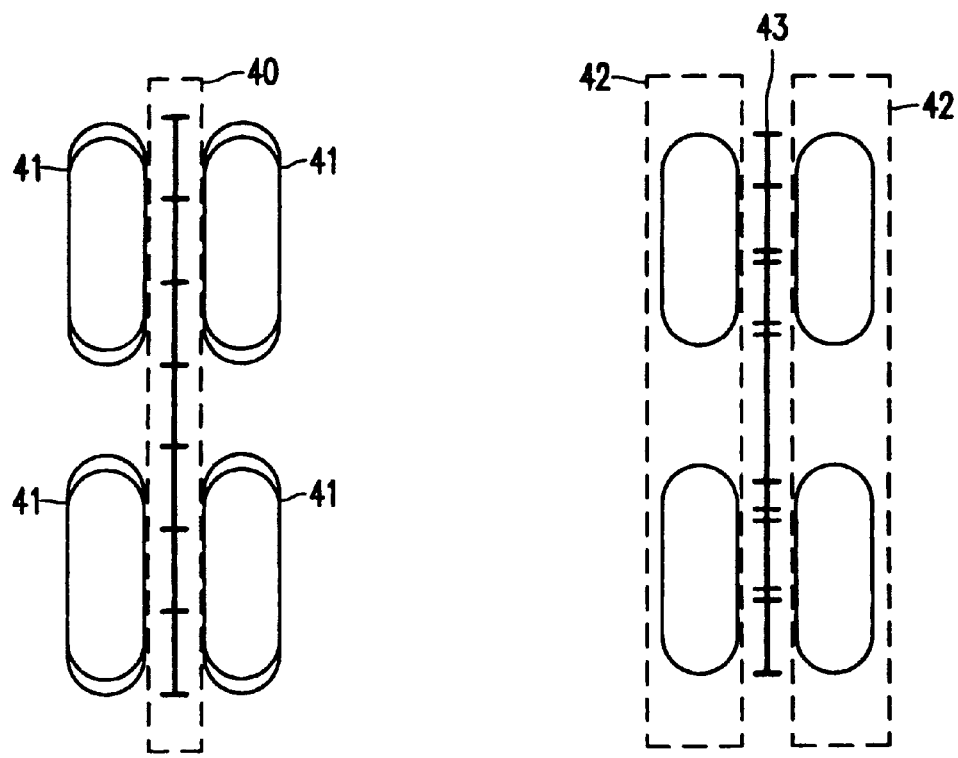
FIG. 2 shows diagrammatically some image processing steps relating to the formation of the combined first and second portions.

FIG. 2 shows diagrammatically some image processing steps performed on combined first and second portions so as to merge the composite image. Each of the sub-images, the combined portions derived therefrom and the composite image includes a matrix of pixels, each pixel having a grey or color value, being the so-called pixel value. FIG. 2 shows notably a combined first portion 40 in which the scale graduation 30 is reproduced. The combined first portion 40 is contained in an image formed by merging sub-images of first portions of individual sub-images in which parts of the scale graduation are reproduced. The sub-images contain image information from the individual X-ray images or the individual X-ray images constitute the sub-images. The combined first portion is merged from successive sub-images and on the basis of the first shift values for separate pairs of sub-images. The first shift values are derived from the first portions of the sub-images in which portions of the scale graduation are reproduced. The shift values are derived notably from correlations of pixel values in said first portions; these pixel values relate to the reproduction of the portions of the scale graduation. It is thus achieved that the scale graduation is reproduced in the combined first portion without serious disturbances. Upon merging of the sub-images on the basis of said first shift values disturbances occur in the reproduction of anatomic information notably due to parallax. This is because the patient, notably the relevant limbs, is/are situated at a slightly different distance from the X-ray source than the scale graduation, because the patient is arranged on the patient table and the ruler 30 is mounted on the patient table. The patient rests on the ruler 30 on the patient table. The disturbed reproduction in the combined first portion 41 is diagrammatically represented by four distorted ovals. FIG. 2 also shows the combined second portion 41 in which anatomic information is reproduced; this is diagrammatically shown in FIG. 2 in the form of four ovals. These ovals diagrammatically represent, for example the upper and lower legs of a patient to be examined. The combined second portion is composed from successive sub-images and on the basis of second shift values for individual successive pairs of sub-images. These second shift values are derived notably from correlations of pixel values relating to the anatomic information. It is thus achieved that the anatomic information in the combined second portion is reproduced in the combined second portion without serious disturbances. However, upon merging of the successive sub-images disturbances occur in the portion relating to the scale graduation which is due notably to parallax. Specifically blurring, doubling or even multiplication of scale marks of the scale graduation occur. This is diagrammatically represented in the disturbed reproduction in the combined second portion 43 of the scale graduation. For example, the legs or the spinal column of the patient and the scale graduation are reproduced mainly in separate portions of the sub-images. This is achieved by reproducing the ruler between the legs of the patient. The ruler and the legs of the patient are situated at different distances from the X-ray source, but are reproduced in separate portions, i.e. the first and second portions, of the sub-images. Separate first and second shift values can thus be derived.

Figure 3:
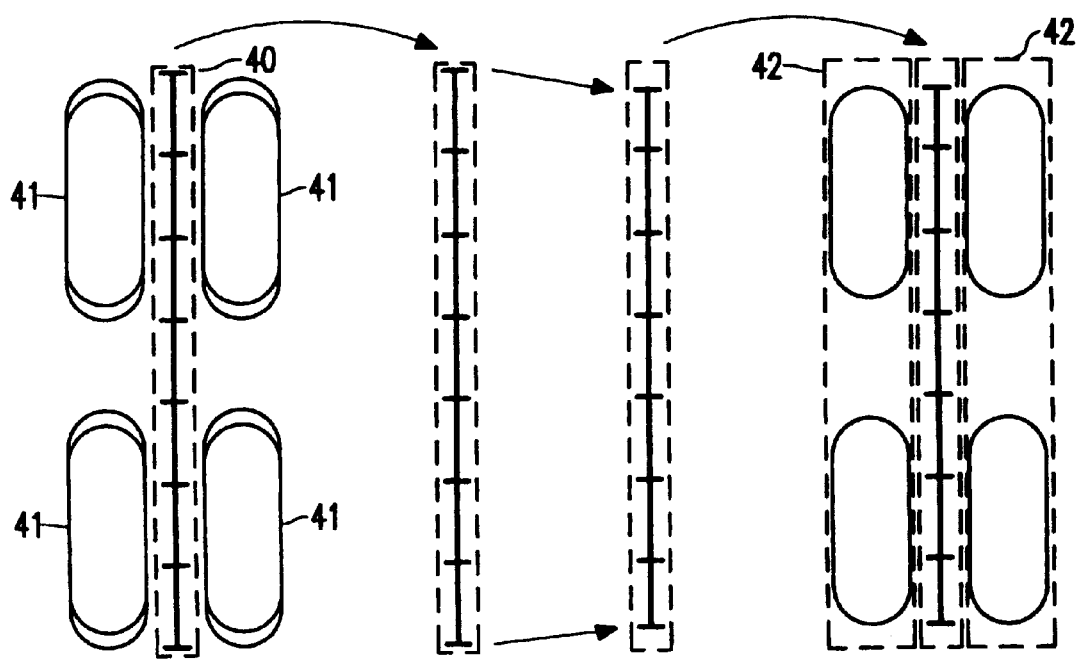
FIG. 3 shows diagrammatically some image processing steps for combining the combined first and second portions so as to form the composite image.

FIG. 3 shows diagrammatically some image processing steps for merging the combined first and second portions so as to form the composite image. The first combined portion 40, in which the scale graduation is reproduced, is separated and compressed in the longitudinal direction. Depending on the actual situation, evidently, the first combined portion could also be expanded. The distorted, i.e. compressed, combined first portion 43 is merged with the combined second portion 42 so as to form the composite image. Upon merging of the sub-images so as to form the first and second combined portions, overlapping portions of the sub-images are superposed; if necessary, pixel values in the overlapping portions are then derived by interpolation of pixel values of the individual sub-images. Upon formation of the first combined portion the overlaps differ slightly from the overlaps of the second combined portion. This is because the first combined portion is merged on the basis of correlations other than those used for the second combined portion. The length of the second combined portion is imparted to the compressed or expanded first combined portion by compressing or expanding the combined first portion on the basis of the ratio of the length of the first combined portion to the length of the second combined portion. The scale graduation can thus be reproduced in the second combined portion without disturbances due to parallax, that is to say with the length corresponding to the length of the second combined portion. The lengths of the first and second combined portions can be readily determined on the basis of the number of columns of the respective matrices of pixels constituting said combined portions.

What is claimed is:

1. A method for composing successive sub-images of a scene into a composite image of the scene, the method comprising:

selecting in each sub-image a respective first portion and a respective second portion, deriving a first shift value for a mutual shift of the successive sub-images from the first portions of the sub-images, wherein the first portions comprise a plurality of pixels, merging the respective first portions of the successive sub-images on the basis of the first shift value so as to form a combined first portion, deriving a second shift value for a mutual shift of the successive sub-images relative to the scene from the second portions of the sub-images, wherein the second portions comprise a plurality of pixels, merging the respective second portions of the successive sub-images on the basis of the second shift value so as to form a combined second portion, distorting the combined first portion on the basis of dimensions of both the combined first portion and the combined second portion, and forming the composite image on the basis of the distorted combined first portion thus obtained and the combined second portion.

2. A method as claimed in claim 1, wherein the combined first portion is distorted on the basis of a ratio of dimensions of the combined first and second portions.

3. A method as claimed in claim 1 wherein said first portions contain mainly image information, and said second portions represent mainly a scale graduation.

4. A method as claimed in claim 1, wherein said distorting of the combined first portion includes compression or expansion in a longitudinal direction of the combined first portion.

5. A method as claimed in claim 1, wherein the step of selecting of first and/or second portions from the sub-images is on the basis of visual inspection of image information of the sub-images.

6. A method as claimed in claim 1, wherein the sub-images contain image information of respective X-ray images.

7. An image composition method for composing successive sub-images of an elongate scene into a composite image comprising composing a first combined image from the successive sub-images on the basis of first mutual shifts between the successive sub-images, wherein the sub-images comprise a plurality of pixels, composing a second combined image from the sub-images on the basis of second mutual shifts between the successive sub-images, distorting the first combined image on the basis of the dimensions of the first combined image and the second combined image, and merging the distorted first combined image and the second combined image so as to form the composite image of the elongate scene.

8. A method for composing sub-images formed of an elongate scene into a composite image of the elongate scene, the method comprising:

selecting in each sub-image a plurality of portions, deriving a plurality of mutual shifts relative to the scene from the plurality of portions of respective sub-images, wherein the portions comprise a plurality of pixels, merging corresponding portions of respective sub-images so as to form a plurality of combined portions on the basis of the mutual shifts of the relevant sub-images, distorting the plurality of combined portions so as to form a plurality of distorted portions, and merging the plurality of distorted portions so as to form the composite image.

9. A method for composing successive sub-images of a scene into a composite image of the scene, the method comprising:

selecting in each sub-image a respective first portion and a respective second portion, deriving a first shift value for a mutual shift of the successive sub-images from the first portions of the sub-images, wherein the first portions represent mainly a scale gradation, merging the respective first portions of the successive sub-images on the basis of the first shift value so as to form a combined first portion, deriving a second shift value for a mutual shift of the successive sub-images relative to the scene from the second portions of the sub-images, wherein the second portions represent mainly image information, merging the respective second portions of the successive sub-images on the basis of the second shift value so as to form a combined second portion, distorting the combined first portion on the basis of dimensions of both the combined first portion and the combined second portion, and forming the composite image on the basis of the distorted combined first portion thus obtained and the combined second portion.

10. The method of claim 9 wherein the combined first portion is distorted on the basis of a ratio of dimensions of the combined first portion and the combined second portion.

11. A method as claimed in claim 9, wherein said distorting of the combined first portion includes compression or expansion in a longitudinal direction of the combined first portion.

12. A method as claimed in claim 9, wherein the first portion or the second portion are selected from the sub-images on the basis of visual inspection image information of the sub-images.

13. The method of claim 1 wherein the step of selecting a respective first portion and a respective second portion is such that the mutual shifts of successive sub-images is substantially constant within the selected first portions or within the selected second portions.

* * * * *